United States Patent
Wo et al.

(10) Patent No.: US 8,226,826 B2
(45) Date of Patent: Jul. 24, 2012

(54) COMPACT DISK BASED SYSTEM FOR SEPARATING IMMUNOMAGNETIC BEAD LABELED PARTICULATES AND METHOD THEREOF

(75) Inventors: Andrew M. Wo, Taipei (TW); Chen-Lin Chen, Taipei (TW); Ken-Chao Chen, Taipei (TW); Yu-Cheng Pan, Taipei (TW)

(73) Assignee: National Taiwan University, Taipei (TW)

( * ) Notice: Subject to any disclaimer, the term of this patent is extended or adjusted under 35 U.S.C. 154(b) by 504 days.

(21) Appl. No.: 12/457,918

(22) Filed: Jun. 25, 2009

(65) Prior Publication Data
US 2010/0227379 A1 Sep. 9, 2010

(30) Foreign Application Priority Data
Mar. 3, 2009 (TW) ................................ 98106786 A

(51) Int. Cl.
*B01D 35/06* (2006.01)
*C12M 1/34* (2006.01)

(52) U.S. Cl. .......... 210/223; 210/695; 422/72; 422/415; 422/506; 422/533; 422/537; 435/4; 435/287.2; 435/287.3; 435/173.9; 436/45; 436/177; 436/526; 494/37; 494/66; 494/84; 494/85

(58) Field of Classification Search .................. 210/695, 210/223; 422/72, 415, 506, 533, 537; 435/4, 435/287.2, 287.3, 173.9; 436/45, 177, 526; 494/37, 66, 84, 85
See application file for complete search history.

(56) References Cited

U.S. PATENT DOCUMENTS

| | | | | |
|---|---|---|---|---|
| 5,565,105 A | * | 10/1996 | Thakor | 210/695 |
| 6,723,510 B2 | * | 4/2004 | Lubenow et al. | 435/174 |
| 8,039,249 B2 | * | 10/2011 | Wo et al. | 435/287.2 |
| 2005/0221281 A1 | * | 10/2005 | Ho | 435/287.1 |

* cited by examiner

*Primary Examiner* — David A Reifsnyder
(74) *Attorney, Agent, or Firm* — Rosenberg, Klein & Lee

(57) ABSTRACT

Disclosed is a disk based system for separating at least two types of particulates contained in a sample fluid. The system includes a disk-like carrier board and a magnetic attraction unit. The disk-like carrier board forms at least one flow channel structure, which includes an inner reservoir, at least one separation chamber, and at least one outer reservoir arranged in sequence from a geometric center of the disk-like carrier board to an outer circumferential rim of the disk-like carrier board. A method of separation carried out with the system includes introducing the sample fluid into the inner reservoir and then rotating the disk-like carrier board to induce a centrifugal force. The sample fluid contains particulates that are labeled with immunomagnetic beads and the labeled particulates are attracted by the magnetic force generated by the magnetic attraction unit to retain in the inner reservoir or the separation chamber. Particulates not labeled with the immunomagnetic beads and contained in the sample fluid move with the sample fluid to the outer reservoir.

22 Claims, 9 Drawing Sheets

COMPACT DISK BASED SYSTEM FOR SEPARATING IMMUNOMAGNETIC BEAD LABELED PARTICULATES AND METHOD THEREOF

FIELD OF THE INVENTION

The present invention relates to separation of at least two types of particulates in a fluid sample, and in particular to a compact disk based system for separating particulates labeled with immunomagnetic beads and a method thereof.

BACKGROUND OF THE INVENTION

Techniques for separation of particulates are of wide applications among which one commonly seen application is to separate cells. In biomedical science, detection and quantification of cancer cells or rare cells present in body fluids are regarded as a potential indicator for clinical diagnoses, prognostication, and biomedicine research. For example, circulating tumor cells (CTC) are rare in the blood of patients with metastatic cancer, and it is possible to monitor the response of CTC to adjuvant therapy. Other examples include detections of fetal cells contained in maternal blood, cells contained in whole blood, and endothelial colony forming cells (ECFC) contained in umbilical cord blood (UCB).

Various techniques of particulates separation are now applied in the separation of cells, including fluorescence activated cell separation (FACS), dielectrophoresis (DEP) cell separation, separation techniques that employ massively parallel microfabricated sieving devices, magnetically activated cell separation (MACS), and other techniques that uses optics and acoustics. Among these cell separation techniques, FACS and MACS are most often used.

Although it is often used, FACS suffers several drawbacks, including high cost, system bulkiness, difficulty in disinfection, consuming a great amount of sample in the operation thereof, and having only limited sensitivity in the operation of detection and separation.

Contrary to FACS, MACS is efficient to obtain a major quantity of the target cells in a short period and reduces the consumption of sample. However, these cells must be transferred to a slide or an observation platform before they can be observed with a microscope. Such a process of transfer often leads to a great loss of cells.

U.S. Pat. No. 5,565,105 discloses a magnetocentrifugation method, wherein charged particles are deposited in a rotor board and a magnetic field is vertically applied to the rotor board. When the rotor board is brought into rotation, the charged particles carried by the rotor board are caused to move through the magnetic field, whereby the charged particles are subjected to Lorentz force and separated from non-charged particles.

U.S. Pat. No. 6,723,510 discloses a method for separating particles with minimized particle loss, wherein a detergent containing matrix beads is bound with a sample containing target particles in order to reduce the loss of the target particles in the separation processes.

SUMMARY OF THE INVENTION

In view of the above described, the conventional separation techniques suffer high system cost, bulkiness of system, and extended time cycle of separation operation, and are also disadvantageous in that the sensitivity of detection and separation is constrained, the result of separation is poor, and direct observation cannot be made immediately after separation, which leads to great losses of cells caused by transferring the separated cells to a slide or an observation platform.

Thus, an objective of the present invention is to provide a compact disk based system for separating particulates labeled with immunomagnetic beads, which is low cost, is easy to perform detection and observation, and has reduced cell loss, and the system is applicable to separate, in a fluid sample, at least two types of particulars, which are respectively labeled and not labeled with the immunomagnetic beads.

Another objective of the present invention is to provide a compact disk based system for separating particulates labeled with immunomagnetic beads, which comprises a stepwise channeling configuration to enhance the separation of at least two particulates that are contained in a sample fluid and are respectively labeled and not labeled with immunomagnetic beads.

A further objective of the present invention is to provide a method for separating immunomagnetic-bead-labeled particulates, which enhances the result of separation of at least two particulates that are respectively labeled and not labeled with immunomagnetic beads in order to facilitate subsequent observation.

The solution adopted in the present invention to overcome the problems of the conventional techniques comprises a disk-like carrier board that forms at least one flow channel structure and a magnetic attraction unit. Each flow channel structure comprises an inner reservoir, at least one separation chamber, and at least one outer reservoir, which are arranged in sequence from a geometric center of the disk-like carrier board to an outer circumferential rim of the disk-like carrier board and are in fluid communication with each other through at least one micro flow channel. The magnetic attraction unit is arranged atop the disk-like carrier board and adjacent to the inner reservoir and the separation chamber to generate a magnetic force having a predetermined distribution of intensity and covering the inner reservoir and the separation chamber.

A sample fluid containing at least two types of particulates, which are respectively labeled and not labeled with immunomagnetic beads, is introduced into the inner reservoir of the flow channel structure of the disk-like carrier board. The disk-like carrier board is driven to spin at a first predetermined rotation speed so that the sample fluid is caused by a centrifugal force induced by the spinning of the disk-like carrier board to flow from the inner reservoir through the micro flow channel into the separation chamber with a portion of the immunomagnetic-bead-labeled particulates is attracted by the magnetic force generated by the magnetic attraction unit to retain in the inner reservoir.

When the sample fluid flows through the separation chamber, a remaining portion of the immunomagnetic-bead-labeled particulates that was not attracted by the magnetic force to retain in the inner reservoir is subjected again to the attraction by the magnetic force generated by the magnetic attraction unit to retain in the separation chamber. The non-immunomagnetic-bead-labeled particulates entrain the sample fluid to move through the micro flow channel and are thus collected in at least one outer reservoir formed between the outer circumferential rim of the disk-like carrier board and the separation chamber.

The solution adopted in the present invention is effective in retaining the particulates labeled with immunomagnetic beads in the inner reservoir or the separation chamber by using the magnetic force and allowing the particulates that are not labeled with immunomagnetic beads to move to the outer reservoir by means of a centrifugal force to realize separation.

In respect of manufacturing, the disk-like carrier board can be easily manufactured by means of for example laser machining, CNC machining, micromachining, or injection molding and the material used can be easily acquired, thereby offering an advantage of low cost manufacturing.

In respect of inspection and observation, a user may perform observation directly on the disk-like carrier board without transfer of the particulates, so that the loss of the particulates can be minimized. Excessive sample fluid can be directly discharged through the fluid extraction passage to allow the non-immunomagnetic-bead-labeled particulates to be collected in a more concentrated manner so that the area to be observed can be made small, facilitating the detection and analysis of rare particulates.

Further, the stepwise channeling configuration formed by the inner reservoir and the separation chamber allows the immunomagnetic bead labeled particulates contained in the sample fluid to be captured in a multiple-stepped manner and the result of separation can be even improved through applications of different spinning speeds to the disk-like carrier board. The micro flow channel communicating between the inner reservoir and the separation chamber and the micro flow channel communicating between the separation chamber and the outer reservoir can be of different channel heights, widths, and/or lengths to facilitate the capture of the immunomagnetic bead labeled particulates.

BRIEF DESCRIPTION OF THE DRAWINGS

The present invention will be apparent to those skilled in the art by reading the following description of a preferred embodiment of the present invention and the best mode for carrying out the present invention, with reference to the attached drawings, in which.

DETAILED DESCRIPTION OF THE PREFERRED EMBODIMENTS

Figure 1:
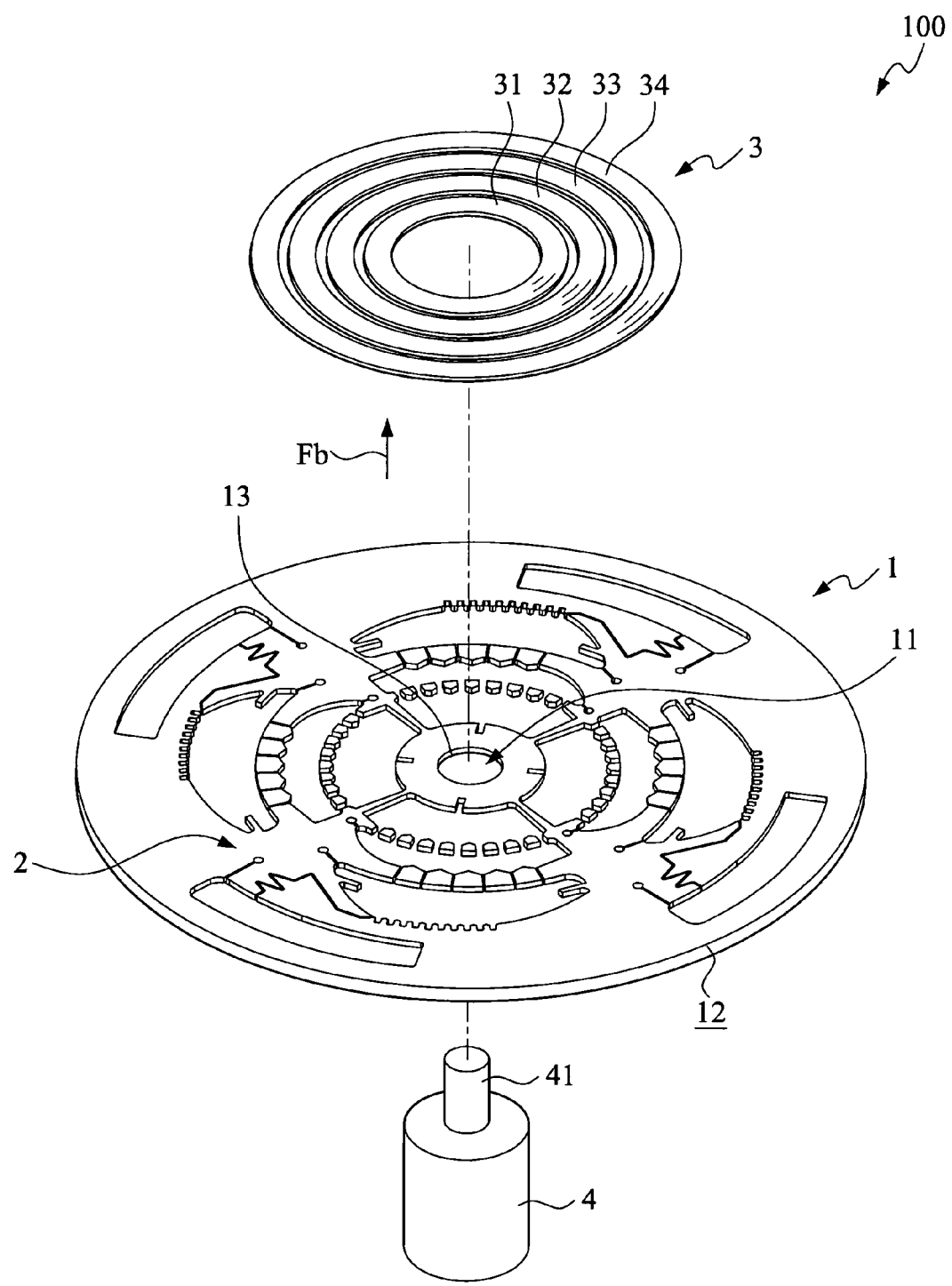
FIG. 1 is a perspective view of a preferred embodiment of the present invention in an exploded form.

With reference to the drawings and in particular to FIG. 1, which shows a perspective view of a preferred embodiment of the present invention, the present invention provides a compact disk (CD) based system, generally designated at 100, for separating particulates labeled with immunomagnetic beads. The system 100 comprises a disk-like carrier board 1 in which at least one flow channel structure 2 is formed for separating at least two types of particulate contained in a sample fluid by using a magnetic force induced by a magnetic attraction unit 3 and a centrifugal force induced by the spinning of the carrier board 1 driven by a driving device 4.

Figure 2:
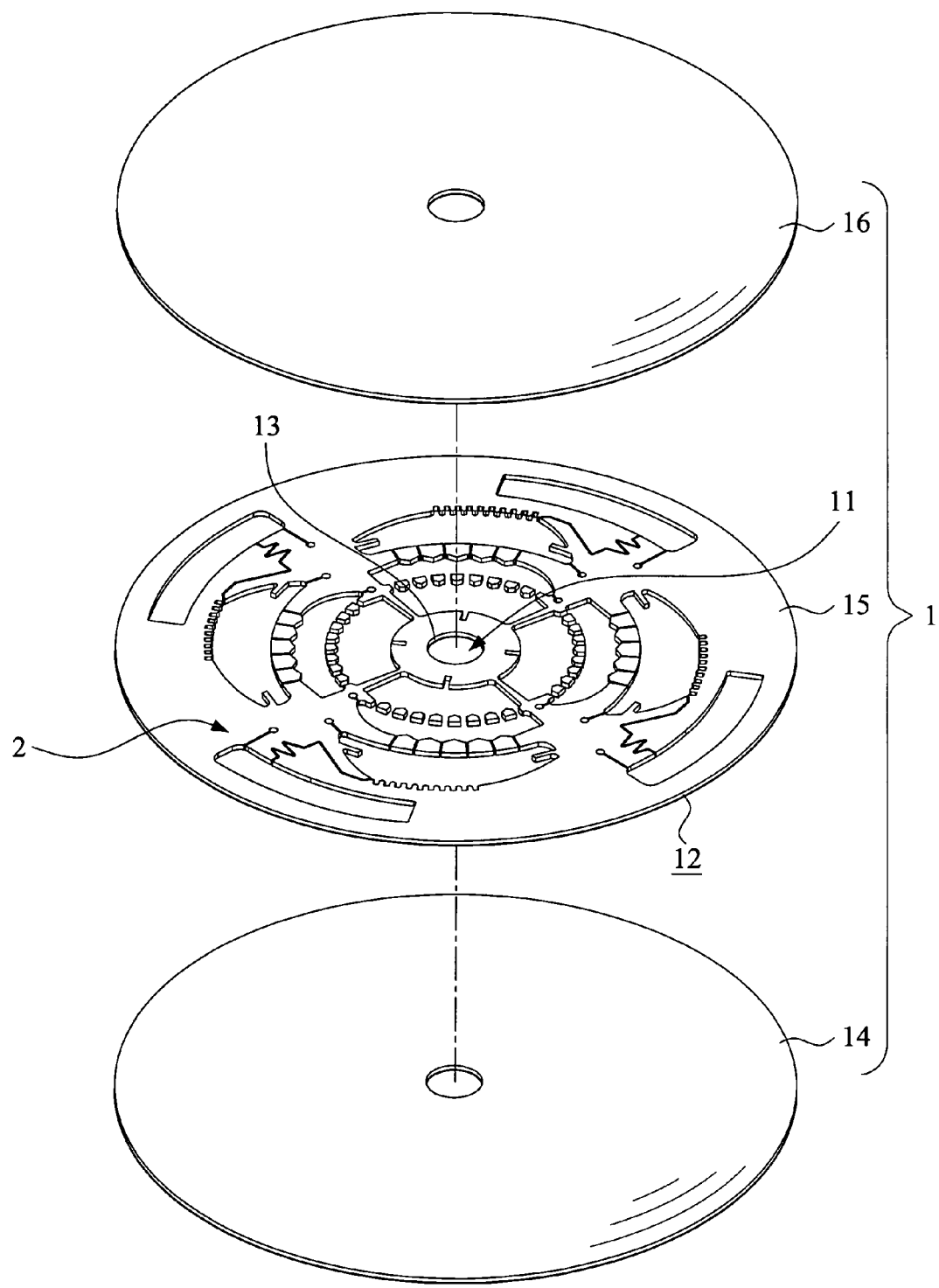
FIG. 2 is an exploded view of a disk-like carrier board in accordance with the present invention.

Also referring to FIG. 2, which shows an exploded view of the disk-like carrier board in accordance with the preferred embodiment of the present invention, the disk-like carrier board 1 has a geometric center 11 and an outer circumferential rim 12. A central hole 13 is defined at the geometric center 11 for coupling to the driving device 4. In the instant embodiment, the disk-like carrier board 1 has a three-layer configuration, which includes, in sequence from the bottom side to the top side, a bottom base layer 14, a middle, flow channel structure layer 15, and a top cover layer 16.

The flow channel structure 2 is formed in the flow channel structure layer 15 of the disk-like carrier board 1. In the instant embodiment, the base layer 14 and the flow channel structure layer 15 are made of acrylic resins, such as polymethylmethacrylate (PMMA), and the cover layer 16 comprises a thin film. In the manufacturing, the flow channel structure layer 15 is processed by $CO_2$ laser machining to form the flow channel structure 2. The flow channel structure layer 15 is then bound to the base layer 14 and the cover layer 16 is applied atop the flow channel structure layer 15 to completely cover and enclose the flow channel structure 2. This way is advantageous by being easy to manufacture, using low cost materials, and reducing manufacturing costs.

Apparently, the flow channel structure layer 15 can alternatively be formed as a stacked multiple-layered structure. Further, the disk-like carrier board 1 can be alternatively made a single-layered structure and the material used is not limited to acrylic reins. The flow channel structure 2 can alternatively formed by employing other types of laser machining, or CNC machining, micromachining, and injection molding.

Figure 3:
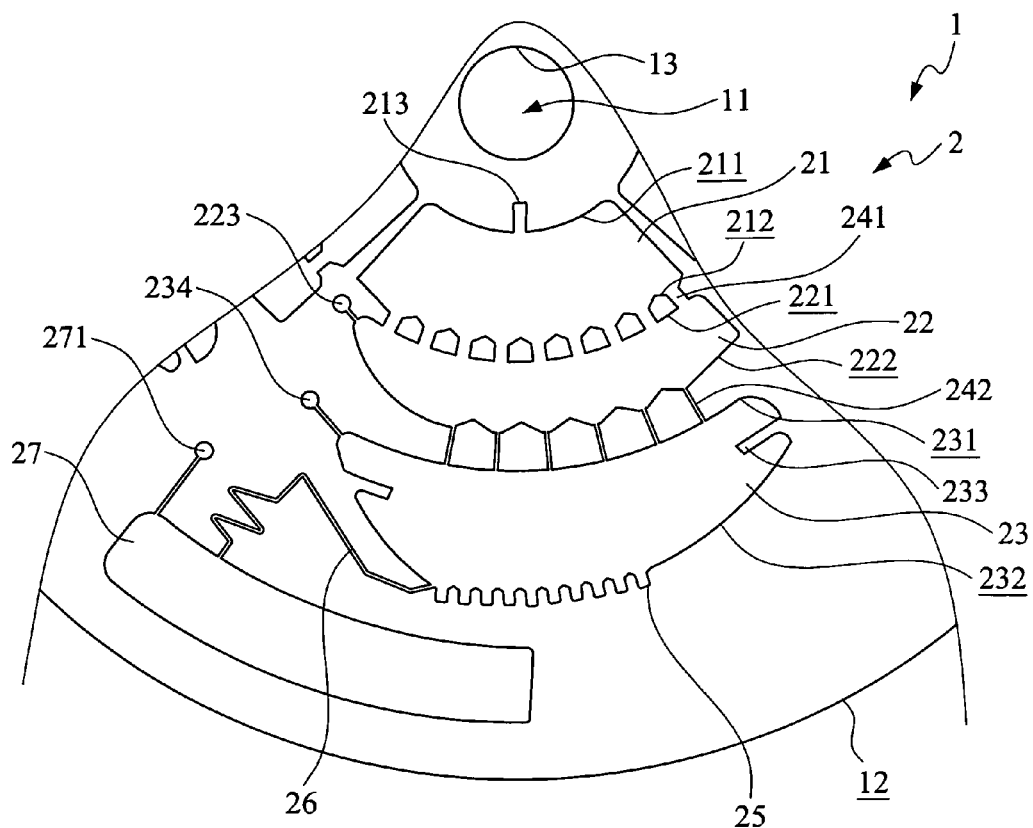
FIG. 3 is a top plan view of a portion of the disk-like carrier board in accordance with the present invention.
Figure 4:
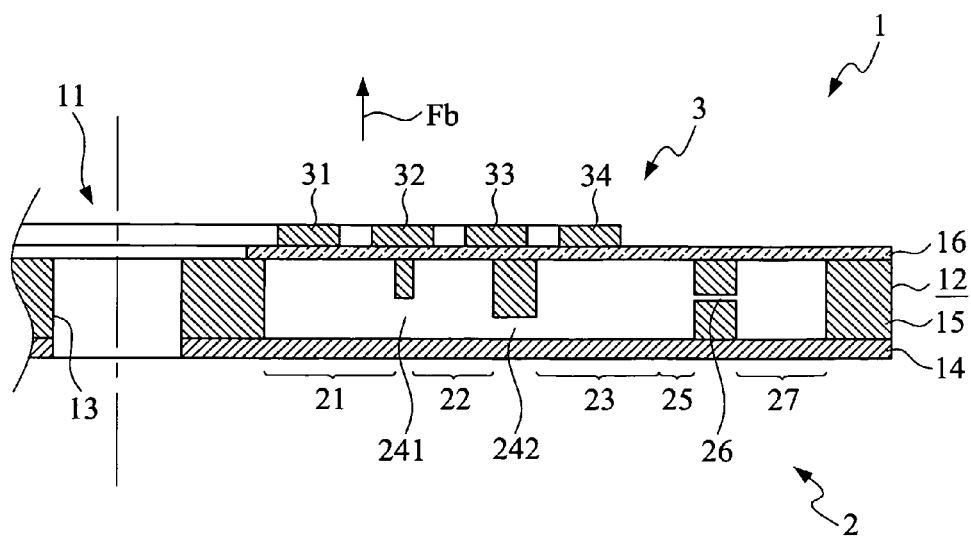
FIG. 4 is a schematic cross-sectional view illustrating the disk-like carrier board of the present invention.

Also referring to FIGS. 3 and 4, which respectively show a top plan view of a portion of the disk-like carrier board and a cross-sectional view of the disk-like carrier board, the disk-like carrier board 1 forms four flow channel structures 2. Each flow channel structure 2 comprises an inner reservoir 21, at least one separation chamber 22 (one separation chamber being used in the instant embodiment), and at least one outer reservoir 23 (one outer reservoir being used in the instant embodiment), which are sequentially arranged in a direction from the geometric center 11 of the disk-like carrier board 1 toward the outer circumferential rim 12.

The inner reservoir 21 has an inner bank 211 and an outer bank 212. The inner bank 211 is adjacent to the geometric center 11 of the disk-like carrier board 1. The inner bank 211 forms a fluid inlet opening 213 that extends in a direction toward the geometric center 11 of the disk-like carrier board 1.

The separation chamber 22 has an inner bank 221 and an outer bank 222, and forms at least one vent hole 223. The inner bank 221 is in fluid communication with the outer bank 212 of the inner reservoir 21 through micro flow channels 241, so as to form a stepwise channeling structure with respect to the inner reservoir 21.

The outer reservoir 23 has an inner bank 231 and an outer bank 232, and forms a pair of reverse flow baffles 233 and at least one vent hole 234. The inner bank 231 is in fluid communication with the outer bank 222 of the separation chamber 22 through micro fluid channels 242. The outer bank 232 is adjacent to the outer circumferential rim 12 of the disk-like carrier board 1 and defines at least one collection bin 25.

The outer reservoir 23 is also in fluid communication with a fluid extraction passage 26, which has a section extending in a direction from the outer reservoir 23 toward the geometric center 11 of the disk-like carrier board 1 and is in fluid communication with a fluid collection chamber 27. The fluid collection chamber 27 is arranged between the outer reservoir 23 and the outer circumferential rim 12 of the disk-like carrier board 1.

In a practical application, the micro flow channels 241 that communicate between the inner reservoir 21 and the separation chamber 22 and the micro fluid channels 242 that communicate between the separation chamber 22 and the outer reservoir 23 can be of different channel heights, widths, and lengths.

For those micro flow channels having greater channel height, greater channel width, and/or shorter channel length, particulates can pass easily (an example being the micro flow channels 241 communicating between the inner reservoir 21 and the separation chamber 22 in the instant embodiment). For those micro flow channels having smaller channel height, narrower channel width, and/or greater channel length, particulates pass with difficult (an example being the micro flow channels 242 communicating between the separation chamber 22 and the outer reservoir 23 in the instant embodiment).

With arrangement of different channel heights, widths, and lengths of the micro flow channels, the easiness of particulates to move through the micro flow channels can be modified as desired. This, together with the stepwise channeling structure formed by the inner reservoir 21 and the separation chamber 22, can adjust result of particulate separation for applications in separating particulates of different kinds.

The magnetic attraction unit 3 is arranged atop the disk-like carrier board 1 and close to the separation chamber 22 to generate a magnetic force Fb that has a predetermined distribution of intensity and covers the inner reservoir 21 and the separation chamber 22. The magnetic attraction unit 3 can comprises various magnets, such as a permanent magnet and an electromagnet and, instead of a single piece of magnet, can alternatively comprise an array of properly arranged magnets.

In the instant embodiment, the magnetic attraction unit 3 comprises a plurality of magnetic elements 31, 32, 33, 34. The magnetic elements 31, 32, 33, 34 are ring magnets that are concentrically arranged in order to generate a magnetic force Fb that has a high gradient distribution of magnetic field. Since the magnets have stronger magnetic forces at marginal areas and weaker ones at central areas, the arrangement of multiple magnetic elements is to provide as many marginal areas that have stronger magnetic forces as possible to thereby provide better magnetic attraction.

In the instant embodiment, the driving device 4 is arranged below the disk-like carrier board 1 and comprises a spindle 41 to operatively couple to the central hole 13 of the disk-like carrier board 1 for spinning the disk-like carrier board 1.

Figure 5:
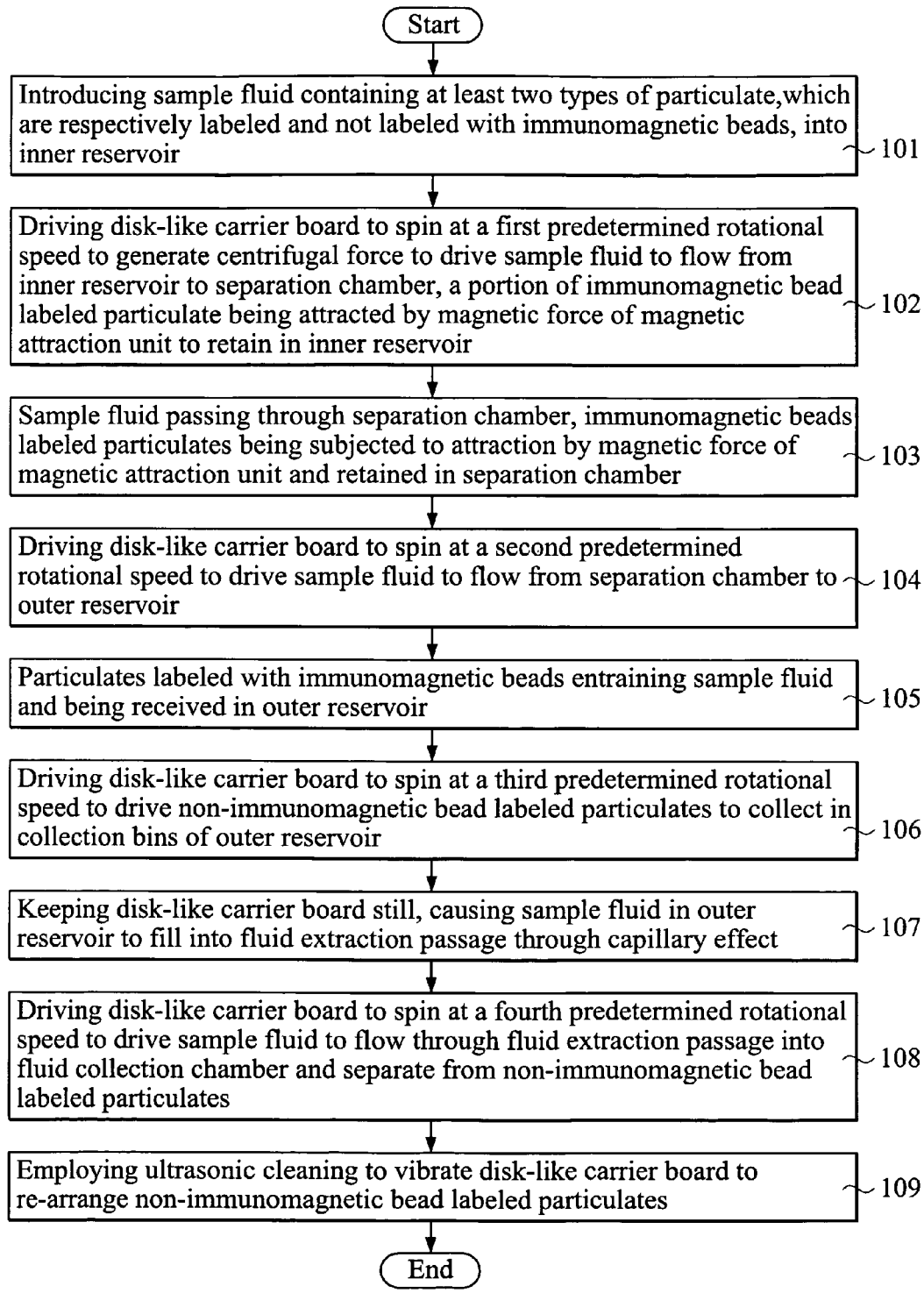
FIG. 5 is a flow chart illustrating a process in accordance with the preferred embodiment of the present invention.
Figure 13:
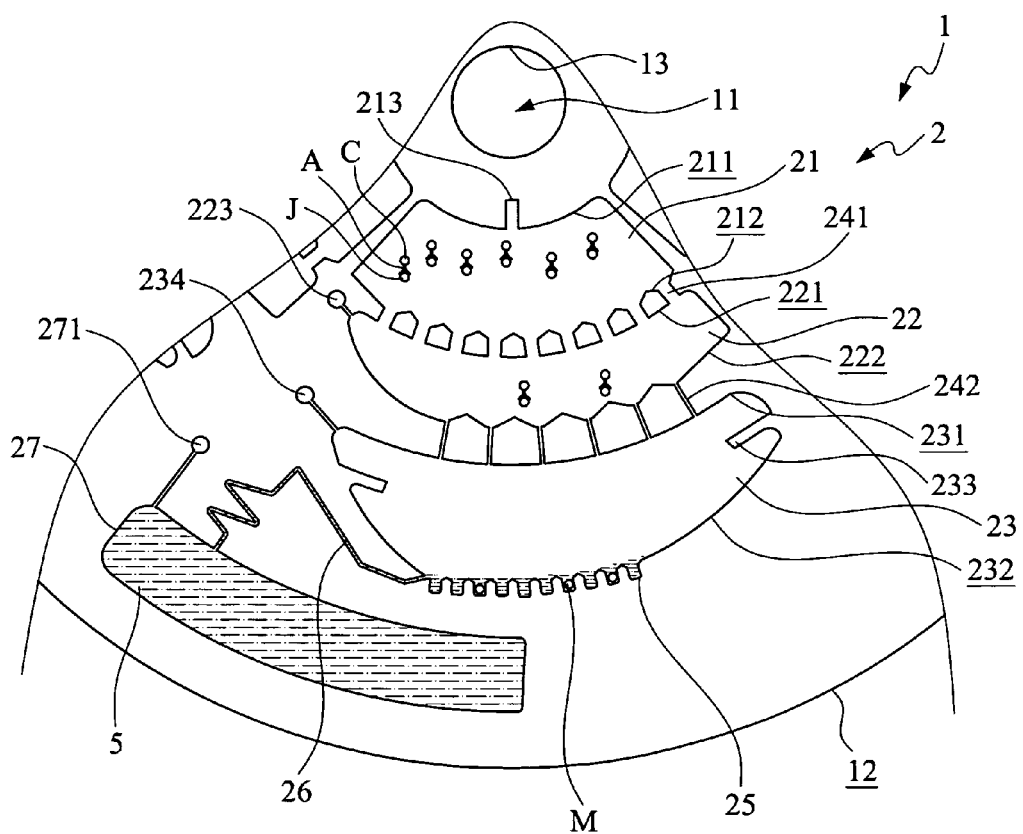
FIG. 13 is a top plan view of a portion of the disk-like carrier board of the present invention illustrating separation of particulates is completed.

Referring to FIG. 5, which shows a flow chart of a process in accordance with the preferred embodiment of the present invention, and reference being also made to FIGS. 6 and 13, the process of the preferred embodiment of the present invention will be explained.

Figure 6:
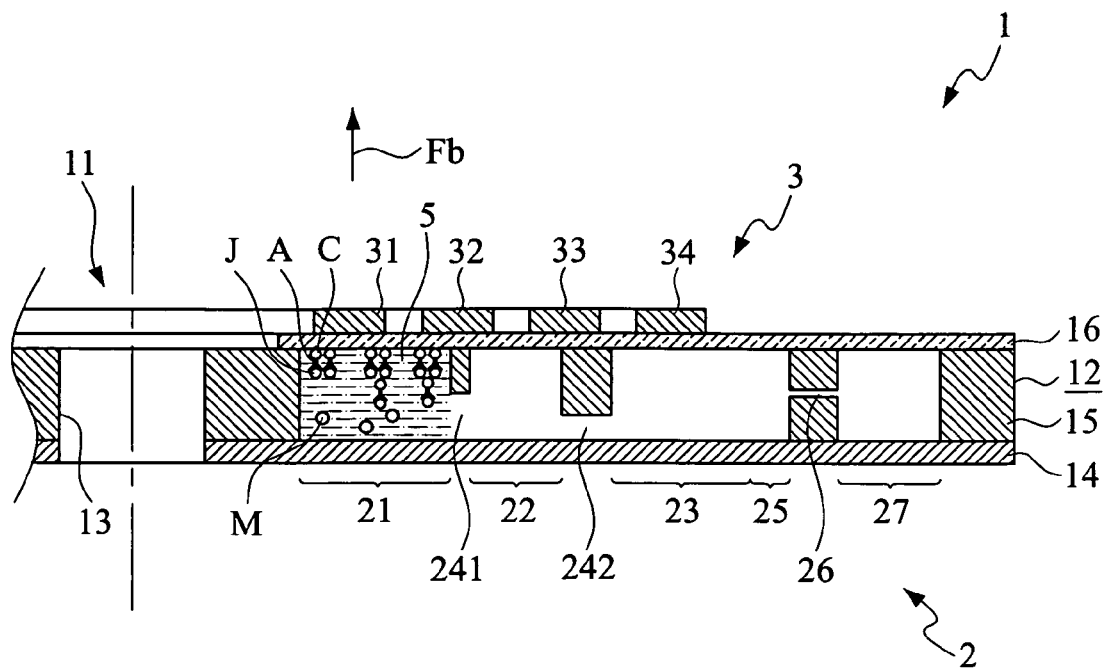
FIG. 6 is a schematic cross-sectional view illustrating the disk-like carrier board of the present invention before being driven to spin.

As shown in FIG. 6, in the instant embodiment, a sample fluid 5 containing two types of particulate is used. One of the particulates is Jurkat cell (J), which is a human lymphoma cell, and the other is MCF7 cell (M), which is a human breast cancer cell. The Jurkat cells J are labeled with immunomagnetic beads C that contain CD45 anti-body A. The MCF7 cells M are not labeled.

Firstly, the sample fluid 5 that contains at least two types of particulate, which are respectively labeled and not labeled with immunomagnetic beads C (namely the Jurkat cells J and the MCF7 cells M) is introduced through the fluid inlet opening 213 into the inner reservoir 21 (Step 101).

Afterwards, the disk-like carrier board 1 is driven to spin at a first predetermined rotational speed V1. The sample fluid 5 is acted upon by a centrifugal force Fc1 induced by the spinning of the disk-like carrier board 1 and flows from the inner reservoir 21 through the micro flow channels 241 to the separation chamber 22 and a portion of the Jurkat cells J that are labeled with the immunomagnetic beads C is attracted by the magnetic force Fb of the magnetic attraction unit 3 to retain in the inner reservoir 21 (Step 102).

Figure 7:
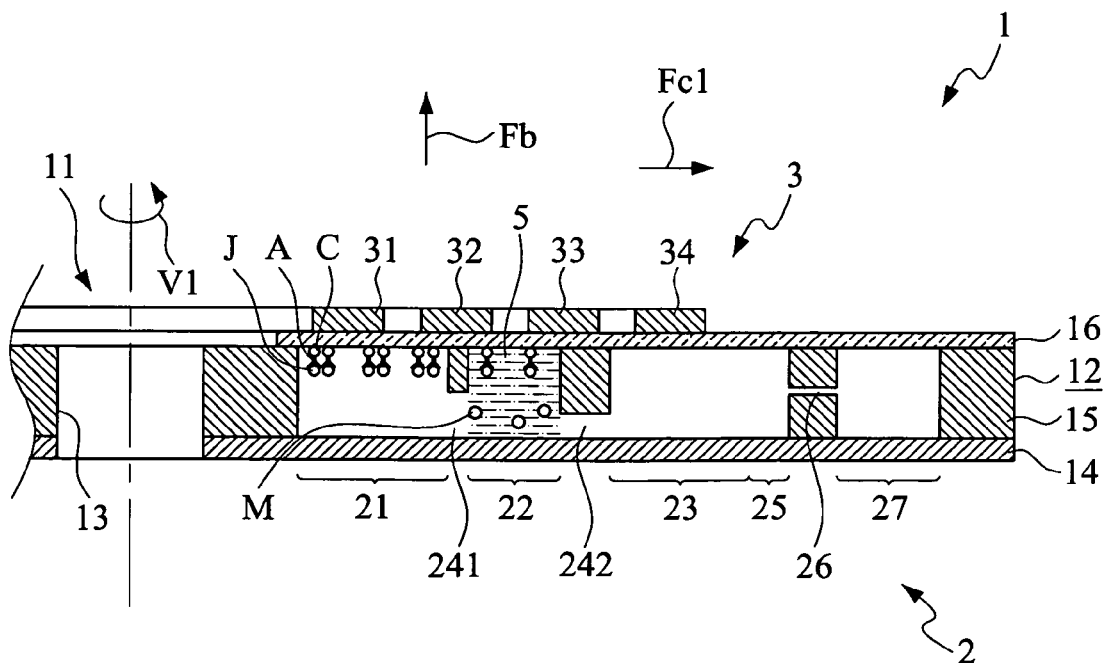
FIG. 7 is a schematic cross-sectional view illustrating the disk-like carrier board of the present invention being driven to spin at a first rotational speed.

Referring to FIG. 7, when the sample fluid 5 passes through the separation chamber 22, the immunomagnetic beads C labeled Jurkat cells J that are not magnetically attracted to retain in the inner reservoir 21 and still entrain the sample fluid 5 are subjected to attraction by the magnetic force Fb of the magnetic attraction unit again and are thus retained in the separation chamber 22 (Step 103).

Figure 8:
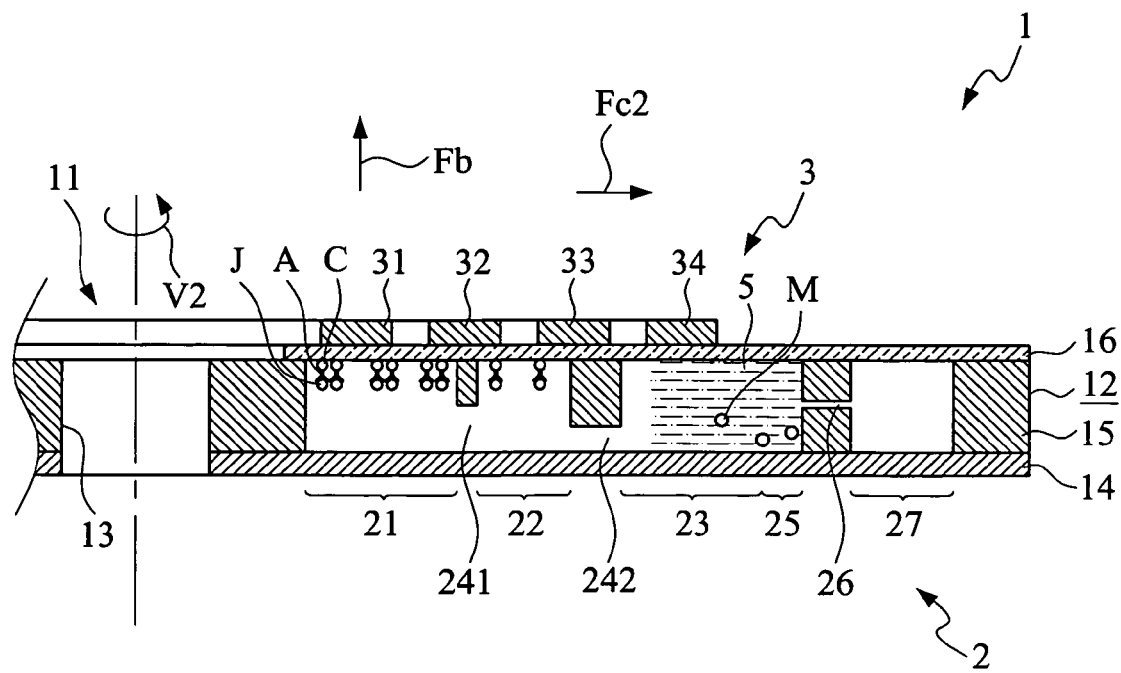
FIG. 8 is a schematic cross-sectional view illustrating the disk-like carrier board of the present invention being driven to spin at a second rotational speed.

The disk-like carrier board 1 is then driven to spin at a second predetermined rotational speed V2 (see FIG. 8) and the sample fluid 5 is acted upon by a centrifugal force Fc2 induced by the spinning of the disk-like carrier board 1 to flow from the separation chamber 22 to the outer reservoir 23 (Step 104). The MCF7 cells M that are not labeled with the immunomagnetic beads C entrain the sample fluid 5 through the micro fluid channels 242 and are thus received in the outer reservoir 23 (Step 105). Since the micro fluid channels 242 that communicate between the separation chamber 22 and the outer reservoir 23 is configured to have a small channel height, a narrow channel width, and a great channel length, the particulates are difficult to pass therethrough. Thus, in the instant embodiment, the second predetermined rotational speed V2 is made greater than the first predetermined rotational speed V1.

Figure 9:
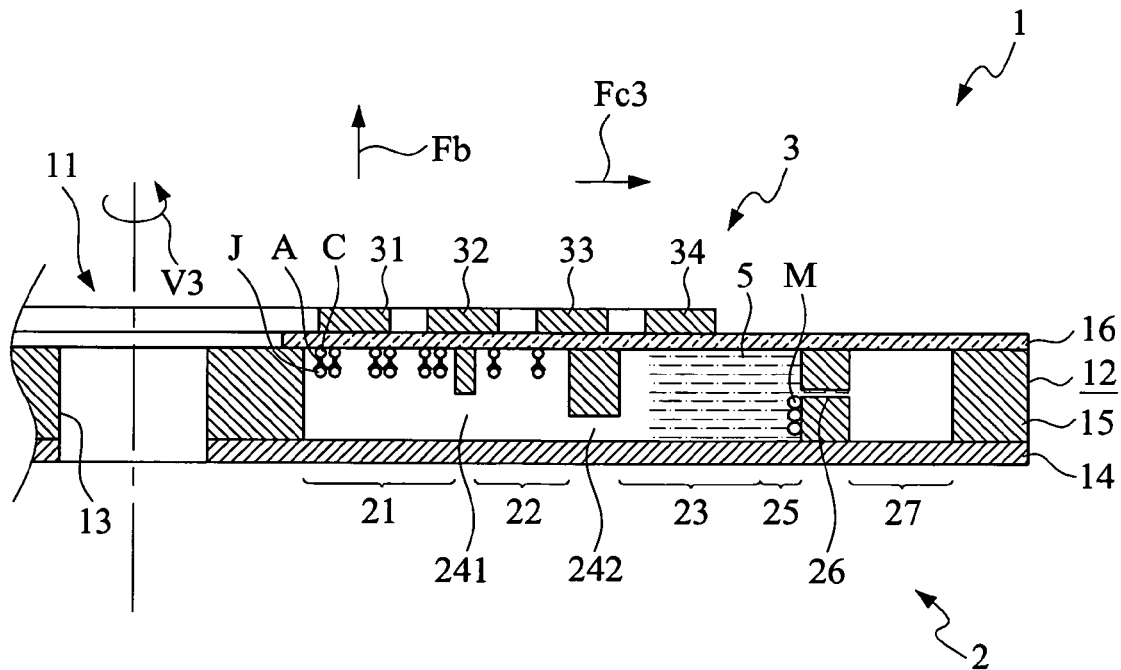
FIG. 9 is a schematic cross-sectional view illustrating the disk-like carrier board of the present invention being driven to spin at a third rotational speed.
Figure 10:
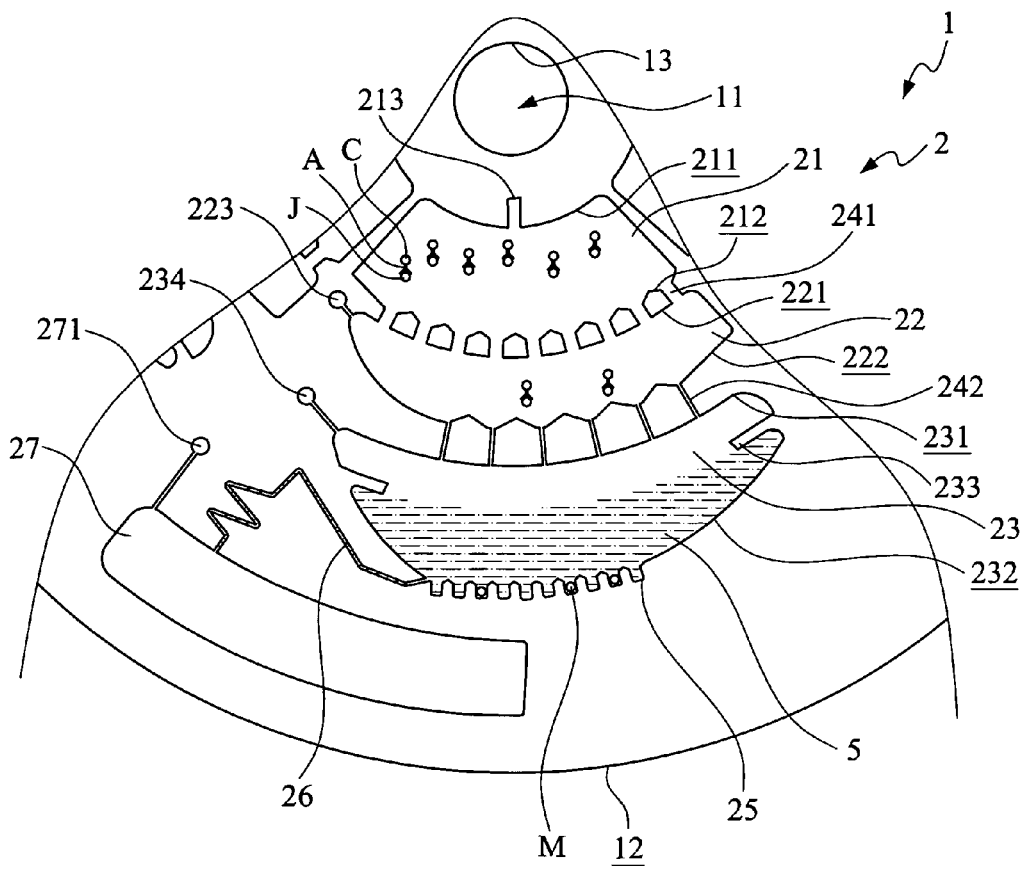
FIG. 10 is a top plan view of a portion of the disk-like carrier board of the present invention illustrating when the disk-like carrier board is kept still.
Figure 11:
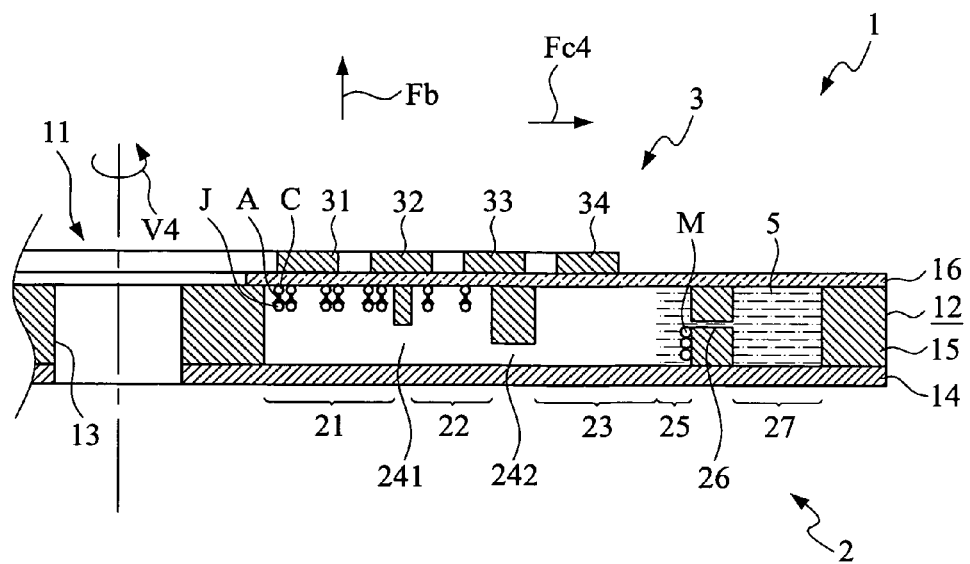
FIG. 11 is a schematic cross-sectional view illustrating the disk-like carrier board of the present invention being driven to spin at a fourth rotational speed.
Figure 12:
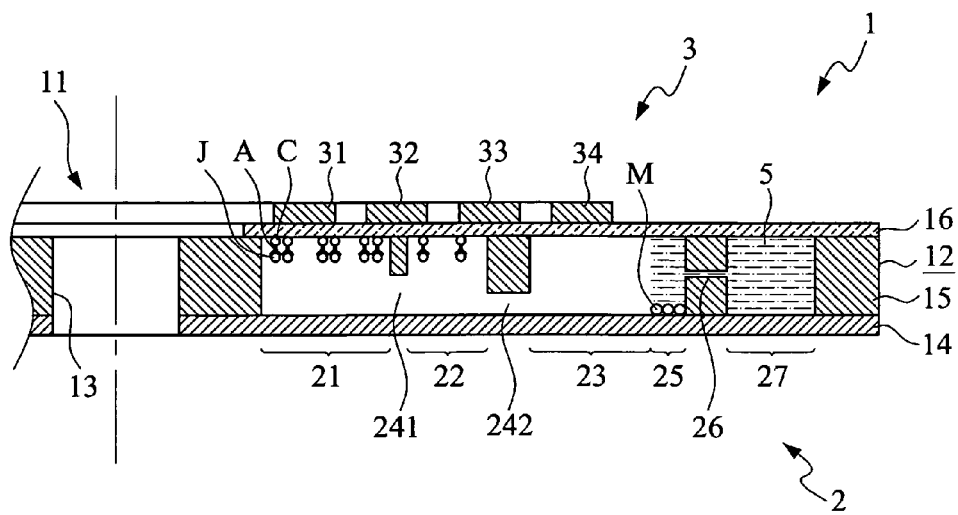
FIG. 12 is a schematic cross-sectional view illustrating the disk-like carrier board of the present invention being subjected to vibration.

Afterwards, the disk-like carrier board 1 is driven to spin at a third predetermined rotational speed V3 that is greater than the second predetermined rotational speed V2 (see FIG. 9) and the sample fluid 5 is acted upon by a centrifugal force Fc3 induced by the spinning of the disk-like carrier board 1 to have the MCF7 cells M that are contained in sample fluid 5 and not labeled with the immunomagnetic beads C collected in the collection bins 25 of the outer reservoir 23 (Step 106).

It is apparent to those skilled in the art that although it is described to spin the disk-like carrier board 1 with three different rotational speeds in sequence, the spinning of the disk-like carrier board 1 is made continuous by timely and sequentially changing the rotational speed during the rotation of the disk-like carrier board 1.

Figure 14:
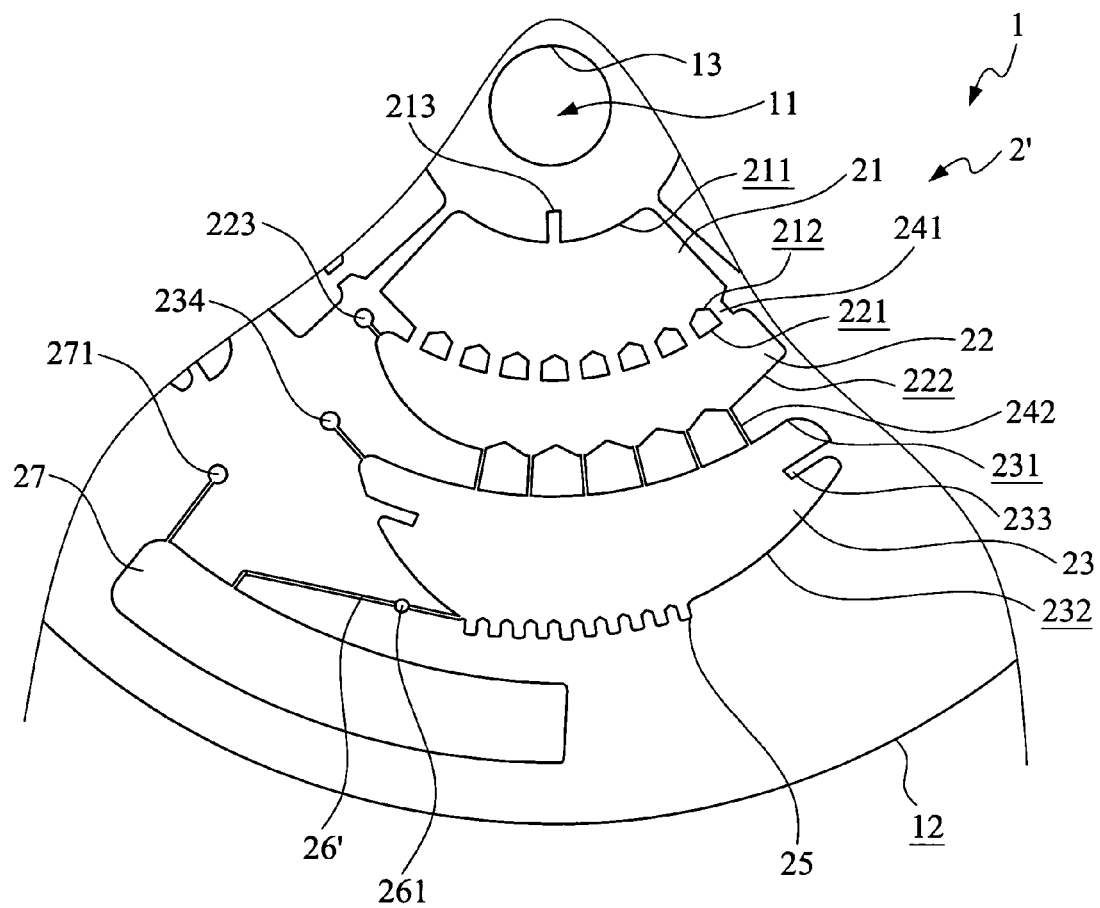
FIG. 14 is a top plan view of a portion of the disk-like carrier board of the present invention illustrating an embodiment where a valve is mounted to a fluid extraction passage.

In the instant embodiment, the fluid extraction passage 26 has a front section that is connected to the outer reservoir 23 and the front section is set in a direction toward the geometric center 11 of the disk-like carrier board 1 in order to prevent the sample fluid 5 and the non-immunomagnetic-bead-labeled MCF7 cells M to directly flow through the fluid extraction passage 26 and into the fluid collection chamber 27 due to the centrifugal force induced by the rotation of the disk-like carrier board 1. An alternative configuration of the flow channel structure, which is labeled 2' (see FIG. 14), can be used instead, wherein at least one valve 261 is arranged on the fluid extraction passage, which is labeled 26', and the same effect of controlling the sample fluid 5 to flow through the fluid extraction passage 26' into the fluid collection chamber 27 can be obtained.

The spinning of the disk-like carrier board 1 is stopped after the MCF7 cells M are collected in the collection bins 25 of the outer reservoir 23. The disk-like carrier board 1 is kept still until the sample fluid 5 in the outer reservoir 23 is caused to fill into the fluid extraction passage 26 through capillary effect (Step 107). Since the outer reservoir 23 is provided with a pair of reverse flow baffles 233, reverse flow of the sample fluid 5 will be stopped during the time period when the sample fluid 5 is kept still, and instead, the sample fluid 5 will fill in the fluid extraction passage 26 and stops at the interface between the fluid extraction passage 26 and the fluid collection chamber 27 due to surface tension and air pressure.

The disk-like carrier board 1 is driven to spin again at a fourth predetermined rotational speed V4 and the spinning of the disk-like carrier board 1 induces a centrifugal force Fc4 that causes the sample fluid 5 to flow through the fluid extraction passage 26 into the fluid collection chamber 27 thereby separating from the MCF7 cells M that are not labeled with immunomagnetic beads C (Step 108).

Finally, ultrasonic cleaning is employed to cause vibration of the disk-like carrier board 1 for making the non-immunomagnetic-bead-labeled MCF7 cells M, which are caused to stick to inside wall surfaces and pile up, detaching from the inside wall surfaces and re-arranged (Step 109) to facilitate subsequent observation and analysis. It is certainly possible to vibrate or shake the disk-like carrier board 1 with other known means.

Although the present invention has been described with reference to the preferred embodiment thereof and the best mode for carrying the invention, it is apparent to those skilled in the art that a variety of modifications and changes may be made without departing from the scope of the present invention which is intended to be defined by the appended claims.

What is claimed is:

1. A disk based system for separating at least two types of particulates, which are respectively labeled and not labeled with immunomagnetic beads, contained in a sample fluid, the system comprising:
    a disk-like carrier board, which has a geometric center and an outer circumferential rim, the disk-like carrier board forming at least one flow channel structure, each flow channel structure comprising:
        an inner reservoir, which is arranged adjacent to the geometric center of the disk-like carrier board for receiving the sample fluid,
        at least one separation chamber, which is arranged adjacent to the inner reservoir and is in fluid communication with the inner reservoir through at least one micro flow channel, and
        at least one outer reservoir, which is arranged between the outer circumferential rim of the disk-like carrier board and the separation chamber and is in fluid communication with the separation chamber through at least one micro flow channel; and
        a magnetic attraction unit, which is arranged atop the disk-like carrier board and adjacent to the inner reservoir and the separation chamber to generate a magnetic force that has a predetermined distribution of intensity and covers the inner reservoir and the separation chamber;
    wherein when the disk-like carrier board spins, the sample fluid is caused by a centrifugal force induced by the spinning of the disk-like carrier board to flow from the inner reservoir through the micro flow channels to the outer reservoir whereby the immunomagnetic bead labeled particulates, when passing through the separation chamber, are attracted by the magnetic force generated by the magnetic attraction unit to thereby remain in the separation chamber, and the non-labeled particulates entrain the sample fluid to flow from the inner reservoir through the micro flow channels to the outer reservoir.

2. The system as claimed in claim 1, wherein the disk-like carrier board comprises a cover layer arranged thereon.

3. The system as claimed in claim 1, wherein the disk-like carrier board comprises a base layer and at least one flow channel structure layer, the flow channel structure being formed in the flow channel structure layer.

4. The system as claimed in claim 1, wherein the flow channel structure of the disk is selectively formed by laser machining, CNC machining, micromachining, and injection molding.

5. The system as claimed in claim 1, wherein the outer reservoir has an outer bank that forms at least one collection bin.

6. The system as claimed in claim 1, wherein the outer reservoir comprises at least one pair of reverse flow baffles for preventing reverse flow of the sample fluid.

7. The system as claimed in claim 1, wherein the micro flow channel communicating between the inner reservoir and the separation chamber and the micro flow channel communicating between the separation chamber and the outer reservoir have different channel heights.

8. The system as claimed in claim 1, wherein the micro flow channel communicating between the inner reservoir and the separation chamber and the micro flow channel communicating between the separation chamber and the outer reservoir have different channel widths.

9. The system as claimed in claim 1, wherein the micro flow channel communicating between the inner reservoir and the separation chamber and the micro flow channel communicating between the separation chamber and the outer reservoir have different channel lengths.

10. The system as claimed in claim 1, wherein the flow channel structure of the disk-like carrier board comprises at least one fluid extraction passage in fluid communication with the outer reservoir to allow the sample fluid to be discharged through the fluid extraction passage.

11. The system as claimed in claim 10, wherein the fluid extraction passage comprises a section extending from the outer reservoir in a direction toward the geometric center of the disk-like carrier board.

12. The system as claimed in claim 10, wherein the fluid extraction passage is set in fluid communication with at least one fluid collection chamber for collecting the sample fluid discharged through the fluid extraction passage.

13. The system as claimed in claim 10, wherein the fluid extraction passage comprises a valve mounted thereto.

14. The system as claimed in claim 1, wherein the magnetic attraction unit comprises a magnetic element selected from the group consisting of permanent magnet and electromagnet.

15. The system as claimed in claim 1, wherein the magnetic attraction unit comprises a plurality of magnetic elements to generate a magnetic force that has a high gradient distribution of magnetic field.

16. A method for separating particulates labeled with immunomagnetic beads, wherein a disk-like carrier board forms at least one flow channel structure thereon, each flow channel structure comprising an inner reservoir arranged adjacent to a geometric center of the disk-like carrier board, at least one separation chamber arranged in fluid communication with the inner reservoir through at least one micro flow channel, and at least one outer reservoir arranged between an outer circumferential rim of the disk-like carrier board and the separation chamber and in fluid communication with the separation chamber through at least one micro flow channel, a magnetic attraction unit being arranged atop the disk-like carrier board and adjacent to the inner reservoir and the separation chamber to generate a magnetic force that has a predetermined distribution of intensity and covers the inner reservoir and the separation chamber, the method comprising the following steps:

(a) introducing a sample fluid containing at least two types of particulates, which are respectively labeled and not labeled with immunomagnetic beads, into the inner reservoir;

(b) spinning the disk-like carrier board with a first predetermined rotation speed so that the sample fluid is caused by a centrifugal force induced by the spinning of the disk-like carrier board to flow from the inner reservoir through the micro flow channel into the separation chamber with a portion of the immunomagnetic-bead-labeled particulates is attracted by the magnetic force that is generated by the magnetic attraction unit and covers the inner reservoir to retain in the inner reservoir;

(c) subjecting a remaining portion of the immunomagnetic bead labeled particulates to attraction by the magnetic force that is generated by the magnetic attraction unit and covers the separation chamber to retain in the separation chamber; and (d) collecting the non-immunomagnetic-bead-labeled particulates, which entrain the sample fluid through the micro flow channel, in the outer reservoir.

17. The method as claimed in claim 16 further comprising, before step (d), a step of spinning the disk-like carrier board with a second predetermined rotational speed to cause the sample fluid to flow from the separation chamber through the micro flow channel into the outer reservoir.

18. The method as claimed in claim 16 further comprising, after step (d), a step of spinning the disk-like carrier board with a third predetermined rotational speed to cause the non-immunomagnetic bead labeled particulates contained in the sample fluid to be collected in at least one collection bin formed in an outer bank of the outer reservoir.

19. The method as claimed in claim 16 further comprising, after step (d), a step of keeping the disk-like carrier board still to have the sample fluid in the outer reservoir filled into at least one fluid extraction passage that communicates with the outer reservoir.

20. The method as claimed in claim 19 further comprising, after the step of filling the sample fluid of the outer reservoir into the at least one fluid extraction passage communicating the outer reservoir, a step of spinning the disk-like carrier board with a fourth predetermined rotational speed to have the sample fluid flowing through the fluid extraction passage into at least one fluid collection chamber in fluid communication with the fluid extraction passage for separation from the non-immunomagnetic bead labeled particulates.

21. The method as claimed in claim 16 further comprising, after step (d), a step of vibrating the disk-like carrier board to have the non-immunomagnetic bead labeled particulates re-arranged.

22. The method as claimed in claim 21, wherein the vibration of the disk-like carrier board is realized through ultrasonic cleaning in order to have the non-immunomagnetic bead labeled particulates re-arranged.

* * * * *